United States Patent [19]
Turner et al.

[11] Patent Number: 5,462,743
[45] Date of Patent: Oct. 31, 1995

[54] SUBSTANCE TRANSFER SYSTEM FOR TOPICAL APPLICATION

[75] Inventors: Josephine S. Turner, Kettleby; D. Gary Murray, Willowdale; John D. Zuccolin, Stouffville; Ruey S. Li, Thornhill, all of Canada

[73] Assignee: Medipro Sciences Limited, Toronto, Canada

[21] Appl. No.: 102,786

[22] Filed: Aug. 6, 1993

Related U.S. Application Data

[63] Continuation-in-part of Ser. No. 969,721, Oct. 30, 1992, abandoned.

[51] Int. Cl.⁶ .................................................. A61F 13/02
[52] U.S. Cl. ........................... 424/448; 424/449; 602/41; 602/46
[58] Field of Search ................................ 424/448, 449; 602/41, 46

[56] References Cited

U.S. PATENT DOCUMENTS

| | | | |
|---|---|---|---|
| 4,262,003 | 4/1981 | Urquhart et al. | 514/291 |
| 4,281,650 | 8/1981 | Spiegelberg | 128/156 |
| 4,711,781 | 12/1987 | Nick et al. | 424/446 |
| 4,801,458 | 1/1989 | Hidaki | 424/443 |
| 4,834,978 | 5/1989 | Nuwayser | 424/448 |
| 4,917,676 | 4/1990 | Heiber et al. | 424/449 |
| 5,064,922 | 11/1991 | Wizk | 604/307 |
| 5,132,115 | 7/1992 | Wolter | 424/448 |

FOREIGN PATENT DOCUMENTS

| | | |
|---|---|---|
| 0242827 | 10/1987 | European Pat. Off. . |
| 8706144 | 10/1987 | Germany . |
| 8709810 | 10/1987 | Germany . |
| 88/01516 | 3/1988 | WIPO . |
| 0410921 | 1/1991 | WIPO . |

*Primary Examiner*—D. Gabrielle Phelan
*Attorney, Agent, or Firm*—Nixon & Vanderhye

[57] ABSTRACT

A substance transfer device for topical or transdermal drug delivery to a living body or collection of fluids from a living body, comprises a layer of skin or wound surface compatible adhesive having a surface for contacting the body, and channels therethrough which provide liquid communication with depots of drug or collection means. These channels form discrete, exposed areas of drug composition or drug delivery means, surrounded by the adhesive. The drug contained in the device does not need to pass through the layer of adhesive before contacting the underlying skin. In one arrangement, particularly suitable for delivery of macromolecular drugs, the channels extend through the entire thickness of the adhesive layer, and communicate with reservoirs of drug.

30 Claims, 6 Drawing Sheets

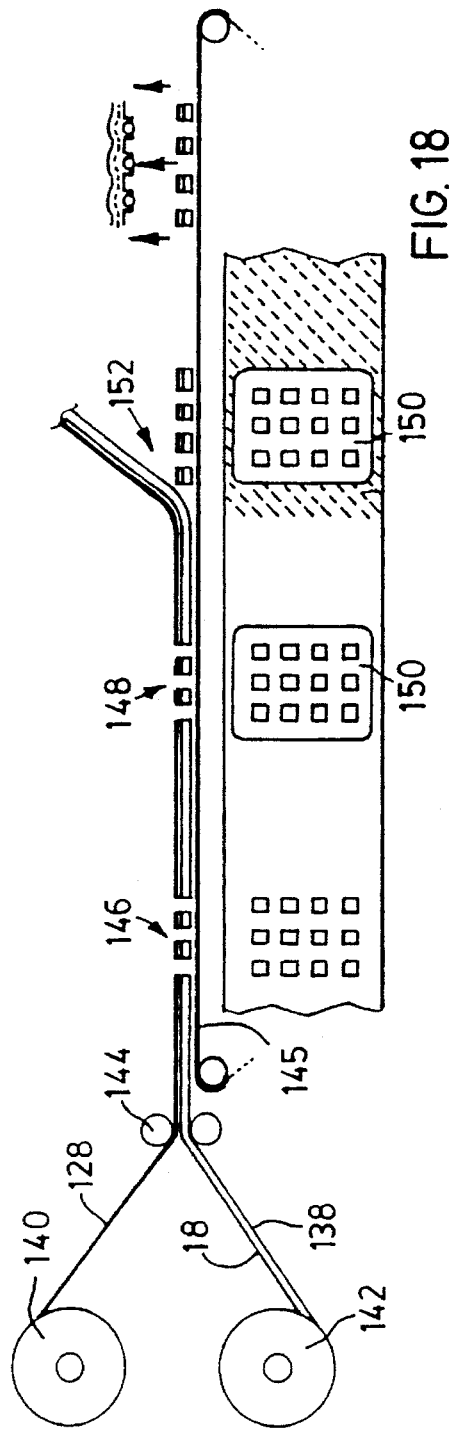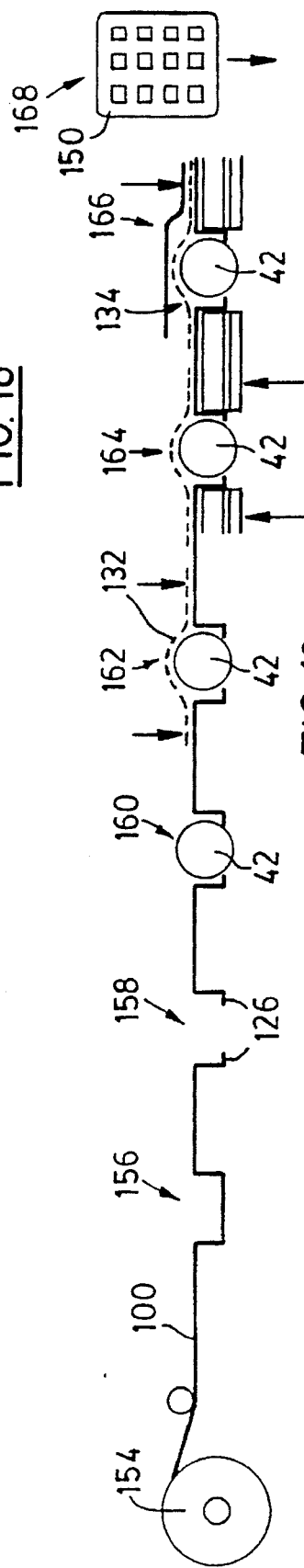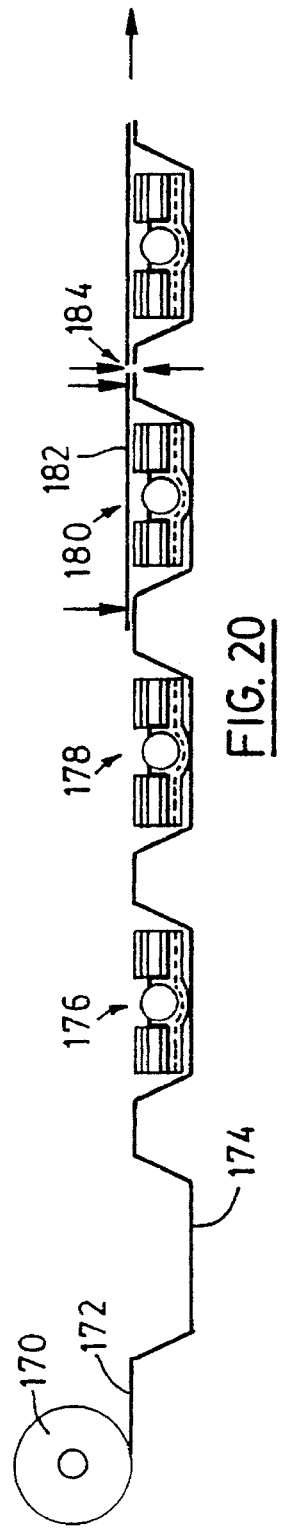
FIG. 18
FIG. 19
FIG. 20

SUBSTANCE TRANSFER SYSTEM FOR TOPICAL APPLICATION

CROSS-REFERENCE TO RELATED APPLICATION

This application is a continuation-in-part of U.S. application Ser. No. 07/969,721 filed Oct. 30, 1992, now abandoned.

FIELD OF THE INVENTION

This invention relates to transdermal and topical drug delivery systems, devices for use therein and methods for their manufacture. It also relates to transdermal substance collection. Such systems and devices are hereinafter collectively called substance transfer systems and devices.

BACKGROUND OF THE INVENTION

Transdermal drug delivery is generally considered to be delivery of a therapeutic agent through the skin of a patient, for distribution of the therapeutic agent within the body by the circulation of the blood. After passing through the outer layers of skin, the therapeutic agent diffuses into the capillaries or tiny blood vessels in the skin, from which it is transported to the circulating blood. Additionally, after having diffused into the skin, the drug may enter into the lymphatic system, and thence be carried to the circulating blood. Topical drug delivery Is generally considered to be delivery to a topical wound, lesion, area affected by a skin disorder etc., of a medicament for the purposes of combatting infections, accelerating wound healing, relieving pain, managing skin disorders etc., by treatment of the localized area.

It may be advantageous to administer some therapeutic agents, such as non-steroidal anti-inflammatory drugs (NSAID), to tissues well below the skin, such as muscles or joints, by topical application to the skin above the area requiring treatment. This is often referred to as either topical or transdermal drug delivery.

A feature which most transdermal drug delivery devices have in common is the provision of a skin compatible adhesive for attaching the device to the skin. For such a device to work effectively, there should be intimate and continuous contact between the patient's skin and the skin contacting layers of the device, to ensure control over the rate of drug delivery. However, the skin contacting adhesive should not deleteriously interfere with the drug's properties, nor with its migration to the skin surface. This means that the choice of adhesive is dictated to a large extent by the choice of drug to be delivered, rather than by allowing a free selection of skin compatible adhesives on the basis of their own inherent properties.

A significant number of pharmaceutical substances are macromolecular in nature, having molecular weights of about 10 kilodaltons or higher, e.g. polypeptides, glycoproteins, etc. Examples of polypeptide and glycoprotein drugs are erythropoietin (30,000 daltons), parathyroid hormone (9,500 daltons), human growth hormone (22,000 daltons), follicle-stimulating hormone (36,000 daltons), interleukin-2 (15,000 daltons), and interferon-alpha (20,000 daltons). Polypeptide and glycoprotein drugs are generally degraded in the stomach and are poorly absorbed in the gastrointestinal tract, so that conventional oral administration is not a viable method of delivery. The normal method of delivery is injection of solutions.

Many polypeptide drugs have very short half-lives once they reach the bloodstream. For example, human growth hormone has a half-life of less than 25 minutes, and parathyroid hormone has a half-life of less than 15 minutes (see R. A. Siegel and Robert Langer, *Pharmaceutical Research*, 1 2 (1984)). Drugs with very short half-lives are generally particularly well suited for a sustained release delivery system such as transdermal delivery, provided that sustained release is not contraindicated by the mode of action of the drug.

Despite the desirability of transdermal delivery of macromolecular polypeptides, there are difficulties which have prevented its commercial realization. The diffusion of macromolecular drugs through conventional skin adhesives is normally too slow to be therapeutically beneficial. The diffusion rate can be increased by causing the adhesive to become grossly swollen with a solvent for the drug, but this will impair its adhesion properties. In addition, drugs of molecular weight over about 500 daltons pass through the skin with great difficulty. Passage of individual macromolecular drugs through the skin is normally prohibitive because of their large size. Even smaller polypeptide drugs, such as luteinizing hormone-releasing factor LHRH (1,200 daltons), LHRH agonists such as nafarelin (1,300 daltons), vasopressin (1,100 daltons), desmopressin (1,100 daltons), ornipressin (1,100 daltons), and octreotide (1000 daltons), can not be expected to penetrate the layers of skin in order to enter the circulating blood in therapeutically useful quantities. The outermost layer of skin, called the stratum corneum and consisting of dead, keratinized epidermal cells, is the main barrier to the entry of drugs into the body by transdermal delivery.

At least partial removal of the stratum corneum at the area to which such macromolecular drugs are to be delivered may well be necessary.

There is also a need in the marketplace for devices which collect substances from a mammalian body, over an extended period of time, for subsequent analysis. Such devices could usefully be provided in the form of adhesive patches for application to a subject's skin and later removal, and containing a form of collection reservoir into which substances from the body migrate. These are useful in monitoring glucose levels, etc., and in detecting illegal substance use.

SUMMARY OF THE INVENTION

It is an object of the present invention to provide a substance transfer device such as a transdermal drug delivery system and device which at least partially reduces the aforementioned disadvantages.

It is a further object of the invention to provide manufacturing processes for making such devices.

The present invention provides, from one aspect, a drug delivery device in which the drug to be delivered, transdermally or topically, makes contact with the body surface at the location of delivery without the interposition of a layer of skin-compatible adhesive between the drug and the body surface. At the same time, the device is sufficiently firmly adhered to the body surface at the desired location, so that no significant breaking of contact between the drug-carrying area and the body surface occurs even as the body surface changes shape and flexes. This is accomplished by providing at least one channel extending through the entire thickness of the adhesive layer, and by means of which the drug is delivered to the body surface. The body-contacting surface of the device is of appropriate size and contour for maintenance of continuous adhesion to chosen body surface. The mouths of the channels at the skin contacting side are surrounded by skin or wound surface compatible adhesive areas of sufficient adhesive strength to maintain the necessary intimate contact of the drug area and the body surface for continuous drug delivery thereto. Any need for the drug carrying surface areas of the device to be adherent to the wound surface or skin surface is consequently eliminated.

With the device of the present invention, the skin compatible adhesive can be chosen mainly on the basis of its own desirable properties, with little regard for its permeability or compatibility properties with respect to the drug to be delivered. The drug no longer needs to migrate or diffuse through the adhesive, in order to achieve effective delivery to the underlying body.

Where the device is one for substance collection from the body, a similar arrangement of channels through the adhesive layer is provided, into which the substance can enter without passing through the adhesive.

Thus according to the present invention, there is provided a topically applicable substance transfer device for transdermal or topical transfer of substances to and from a living body, said device having an inner surface for body contact, and further comprising:

- a layer of skin compatible adhesive having an inner surface for body contact;
- at least one channel extending through the layer of adhesive, and having an inner opening at the inner surface of the device;
- a substance depot in liquid communication with the inner opening of said at least one channel and adapted to transfer substance to and from said opening;
- said inner surface of the device being comprised of discrete areas constituted respectively by the inner opening of said at least one channel and by the inner surface of said adhesive layer.

BRIEF DESCRIPTION OF THE DRAWINGS

FIGS. 18, 19 and 20 are diagrammatic process flow sheets illustrating a preferred manufacturing process for the manufacture of the embodiment of the invention illustrated in FIGS. 14 and 15.

In the figures, like reference numerals indicate like parts.

DESCRIPTION OF THE PREFERRED EMBODIMENTS

Figure 1:
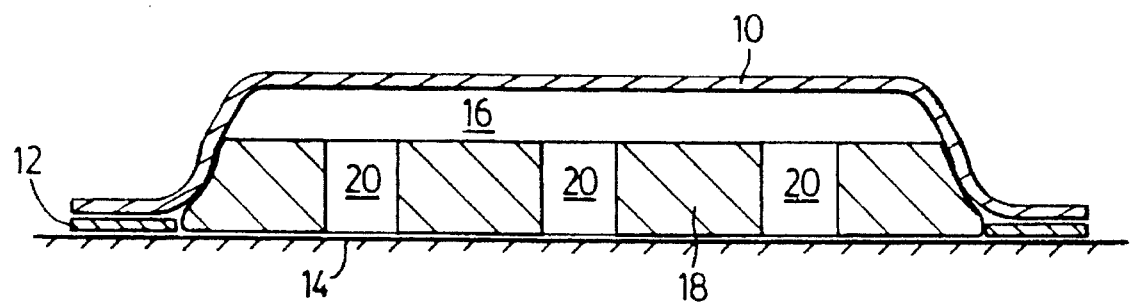
FIG. 1 is a diagrammatic cross-sectional representation of a first preferred embodiment of a drug delivery device according to the present invention, in place on a patient's skin.

The preferred devices of the invention have a plurality of said channels, the inner openings of which are each surrounded by the inner surface of the layer of skin compatible adhesive. Thus the adhesive forms the continuous inner, body-contacting surface of the device, with the channel openings constituting discontinuities therein. Each of the channels constitutes a drug-containing, drug-delivering or substance collecting entity. These channels can extend through the entire thickness of the adhesive layer. In one form, the channels can act as conduits to a substance depot or depots above the adhesive, for example a reservoir of drug-containing liquid, semi-solid or gel. In another form, the channels themselves can be the sole reservoir. In yet another form, the channels can contain discrete bodies or layers, e.g. layers supported on a fibre, of drug-containing material, to which delivery fluid is added immediately prior to use. The devices according to the invention are especially well suited for transdermal delivery of macromolecular drugs, although useful for delivery of drugs of smaller size. The drug can be delivered directly from the channels to the patient's skin, without having to migrate or diffuse through the adhesive layer.

Preferably, the reservoir of drug takes the form of a solution, dispersion or suspension of the drug in a suitable liquid or semi-solid carrier. It may be present simply as a self-supporting filling in the channel, or as a filling in communication with a discrete layer of drug containing liquid or semi-solid, above the adhesive layer. Alternatively the drug solution, dispersion or suspension may be held in the channel in a suitable support such as a porous plastic, open cell foam, pad, fibrous mat etc., chosen in each individual instance with consideration to the viscosity and surface properties of the drug formulation. In order to limit transfer or evaporation of the drug solution or any of the components, there is suitably applied an inert, outer, barrier film, e.g. of foil or polyester plastic, on the side of the device remote from the skin. This film is attached to at least the periphery of the top of the device, and may optionally overlap the adhesive coating to form a rim around the periphery, said rim being provided with a skin compatible adhesive coating to assist in attachment of the device to the patient's skin at the chosen location.

In the simplest form of this general embodiment of the invention, the reservoir of liquid or semi-solid containing the drug will directly contact the sides of the channels through the adhesive layer, and there may be a tendency for the drug or other drug formulation materials contained in the reservoir to diffuse into the body of the adhesive layer. This may affect the adhesive properties and biocompatibility of the adhesive, and may also reduce the effectiveness of drug delivery. These effects can be mitigated by appropriate choice of the consistency and type of the adhesive layer. Otherwise, however, there are very few criteria which the skin compatible adhesive layer needs to meet for use in the present invention. Examples of suitable skin compatible adhesives for use in the present invention include adhesives chosen from well known classes of pressure sensitive adhesives (polyacrylates, polyisobutylene, silicone and the like). One specific example is FLEXcon H566 from The Flexcon Company Incorporated. Such adhesives are merely examples, however, and many other types can be used.

The liquid or semi-solid reservoir containing the drug may take a variety of different forms. For example, it may be a semi-permeable membrane-enclosed capsule, or a packing material in the channel which supports the drug in solution or dispersion. The packing may be of porous plastic, e.g. open cell foam, or fibres or the like holding the liquid drug. Alternatively, liquid or semi-solid reservoirs may be constituted by bodies of predetermined shape, such as spherical, cylindrical, ovoid etc. Such bodies of predetermined shape preferably have a downwardly convex bottom surface to protrude beyond the surface of the adhesive and thereby improve contact with the skin after application.

The formation of appropriate channels through the layer of skin compatible adhesive can be accomplished in any number of ways. One arrangement for providing suitable channels through the adhesive layer is to incorporate therein discrete sections of open cell foam at the time of producing the adhesive layer so that at least some of the open cells provide adhesive-free channels for the passage therethrough of macromolecular or other drug. Another method is to incorporate into the skin compatible adhesive layer at the time of manufacture sections of a matrix of fibres or fused spherical particles, positioned so that at least some of the matrices provide channels of communication between the macromolecular drug reservoir and the underlying skin.

Another arrangement for formation of appropriate channels is to create the channels by removal of matter from a continuous layer.

Depending upon the compatibility between the adhesive and the particular drug formulation, it may be desirable to line the channels through the adhesive with an inert barrier material to limit the diffusion of the drug and other formulation components into the adhesive, and to maintain the integrity of the channels. Silicone films constitute suitable such materials. It may be desirable to have an inert barrier film on the upper surface of the adhesive layer, particularly when there is a reservoir of drug containing material above the adhesive layer. In such an arrangement, it is preferable to join the edges of the channel lining material to the upper barrier film to form a seal, so as completely to prevent diffusion of drug from the reservoir into the adhesive. A cast silicone film provides a satisfactory such top film.

It is frequently desirable to arrange to control the rate of delivery of drugs to the patient's skin surface and, in some cases, to maintain this rate of drug delivery constant. The rate of drug delivery can be controlled by the inherent ability in this invention to vary the area of drug containing liquid or semi-solid in contact with the skin surface, and the concentration of the drug containing liquid.

To accomplish a constant rate of drug delivery, a saturated solution of the drug which also contains undissolved drug particles (solid or liquid) or a layer or coating of the drug, can be used in the drug reservoir. As long as undissolved drug passes into solution at a rate equivalent to the rate of diffusion of dissolved drug into the skin, a steady state will exist and the rate of drug delivery to the patient's skin will be constant.

In yet another alternative, the rate of drug delivery can be maintained constant by placing a semi-permeable membrane around the drug reservoir layer or body.

In yet another alternative utilizing an upper reservoir arrangement, a semi-permeable rate controlling membrane can be placed between the upper reservoir and the openings of the channels at the side remote from the skin, i.e. the upper side.

The application of the transdermal drug delivery device of this general embodiment of the present invention, especially for macromolecular drug delivery to a patient's skin, is preferably preceded by a step of compromising the barrier properties of the stratum corneum, most preferably by removal or partial removal thereof from the location to which the device is to be applied. This can be accomplished, for example, by use of the stratum corneum removal device described in U.S. patent application Ser. No. 07/920,665 Murray et al., filed Jul. 28, 1992, and by use of the device described in U.S. patent application No. 07/973,101, Murray et al., filed Nov. 2, 1992, both now abandoned.

Devices of the invention are also useful for delivery of drugs to mucosal surfaces of the patient's body, for example vaginal, oral and nasal internal surfaces. By suitable choice of adhesive which is compatible with such mucosal surfaces, and adheres sufficiently strongly to them, the devices according to the present invention can be adapted for drug delivery to locations underlying such mucosal-covered surfaces.

It is additionally within the scope of the present invention to provide two or more different types of reservoirs of drug-containing liquid in the same device. Such an array of reservoirs, which is comprised of a set of reservoirs containing a particular drug and having a particular pattern of drug delivery, and a second set of reservoirs with the same drug but having a different pattern of drug delivery, and optionally further sets of reservoirs with the same drug but still different patterns of drug delivery, provides a means for arranging an overall delivery pattern which is pulsatile.

A further arrangement, according to the present invention, is a device having one set of reservoirs with one drug, a second set with a second drug etc. This provides a means for the simultaneous delivery of more than one drug from the same device in cases in which the drugs would be incompatible if they were in communication with each other.

Yet another arrangement, according to the present invention, is the presence, in the same patch, of a set of reservoirs which deliver a drug, and a second set of reservoirs which deliver a non-drug material beneficial to delivery of that drug such as a skin penetration enhancer.

When the reservoirs contain drug in a non-liquid form, the channels through the adhesive layer may contain the drug in dry form, e.g. as a body in the form of a capsule, pill, sphere or the like, distributed in a capillary "framework" as particles, or as a coating on the surface of the "framework" material. Preferably, the bottom surfaces of the capillary "frameworks" protrude slightly below the surface of the adhesive layer. Each such drug delivery body comprises a collection of interconnected capillaries, rather than a simple capillary channel. Optionally, a reservoir layer above the channels may contain the drug in dry form in addition to, or as an alternative to, the drug in the channels. Such arrangements can have extended shelf life because the drug is more stable in undissolved form than in solution form. The drug dissolving liquid is applied to the device immediately prior to its application on the patient's skin, e.g. by applying a liquid-soaked pad to the bottom surface of the device for a brief period of time, or by building into the device a sealed but rupturable pouch containing liquid or a liquid-soaked pad, to be ruptured so that liquid contacts the drug immediately before application. It is preferred in such arrangements to provide a means whereby air exits from the channels as the drug dissolving liquid is absorbed, and whereby air can replace the drug solution in the reservoir as it migrates out, so that a region of reduced pressure which would inhibit drug flow is not created. This can be done, in the case where a liquid soaked pad is used for application to the bottom surface, by providing an air space above the channels.

Devices according to the present invention can also be adapted for use in the transdermal or topical delivery of drugs which need to be made into appropriate liquid formulations by a clinician immediately prior to their administration to a patient. This occurs, for example, with drugs which are stable in solid form but unstable in liquid solution, suspension or dispersion. Then, the clinician can make up the required formulation according to a predetermined recipe, e.g. as a paste or viscous liquid, apply the device to the patient's body surface at the predetermined location, introduce the formulation into the reservoirs of the device so that it can contact the skin via the channels through the adhesive, and close the top of the device with a protective cover.

A specific example of a drug which can advantageously be administered in this way is 5-aminolevulinic acid (5-ALA) which is used in tumour treatment. It is reported to be preferentially absorbed by cancerous body cells and subsequently converted into protoporphyrin IX, a potent natural photosensitizer. Upon subsequent irradiation of the cells which have absorbed these substances, toxic oxygen compounds are generated, which destroy the cancerous cells. Such compounds are best administered to a patient by a skilled, experienced clinician, and the devices of the invention provide an economic, simple but effective way of accomplishing this.

Devices according to the present invention can also be used to administer drugs transdermally to a patient by iontophoretic processes. In these processes, which are known in the art, an electrical current is passed through the reservoir of drug and the patient's body at the required location, to assist in ionic flow of the drug into the patient's body. A grounding electrode is applied to the patient's body, at an appropriate location, to complete the electrical circuit.

Devices according to the present invention can also be used as substance collection means, whereby fluids collected transdermally from within the patient's body are collected over a prolonged period of time, for monitoring and analysis. By the transdermal application of appropriate electrotransport technologies, substances can be arranged to flow out through the skin and into collection reservoirs of the device according to the invention for subsequent analysis. This can be used not only for collection of ionic substances, but also for collection of neutral substances such as glucose, which are transported by convective flow caused by movement of ionic compounds.

Automatic electronic monitoring of glucose level can also be arranged, e.g. for automatic compensating insulin provision to a diabetic patient.

Body fluids, especially perspiration fluids, can also be collected by devices of the invention, by passive migration out the body, through the skin, into the channels of the device and thence into collection reservoirs to be used for subsequent analysis. Such body fluids analysis can provide valuable information about previous substance consumption by the patient, e.g. illegal drug use.

SPECIFIC DESCRIPTION OF THE MOST PREFERRED EMBODIMENTS

FIG. 1 of the accompanying drawings shows, in diagrammatic cross sectional form, a conceptual representation of a first preferred embodiment of the transdermal drug delivery device according to the present invention, in place on a patient's skin. This embodiment is specially but not exclusively adapted for transdermal delivery of macromolecular drugs. The device comprises an outer film layer 10 having suitable barrier properties for the drug, drug solvent, and all other components dissolved or suspended in the drug solvent. This is typically a foil laminate, but in some cases a plastic film such as polyester is suitable. The outer film layer 10 is provided with a suitable skin adhesive 12, such as one of the type commonly used with conventional adhesive wound coverings, whereby the film 10 may be attached to the underlying skin surface 14 of the patient.

Immediately below the film 10 is a reservoir 16, of viscous liquid comprising a dispersion, suspension or solution of a drug in an appropriate liquid or semi-solid medium. Between the patient's skin 14 and the drug reservoir 16 is a layer of skin compatible adhesive 18. Through the adhesive layer 18 are provided a series of channels 20, each having a diameter of approximately 2 mm, providing direct communication from reservoir 16 to the patient's skin surface 14. This allows the drug composition to make direct contact with the skin surface 14.

Figure 2:
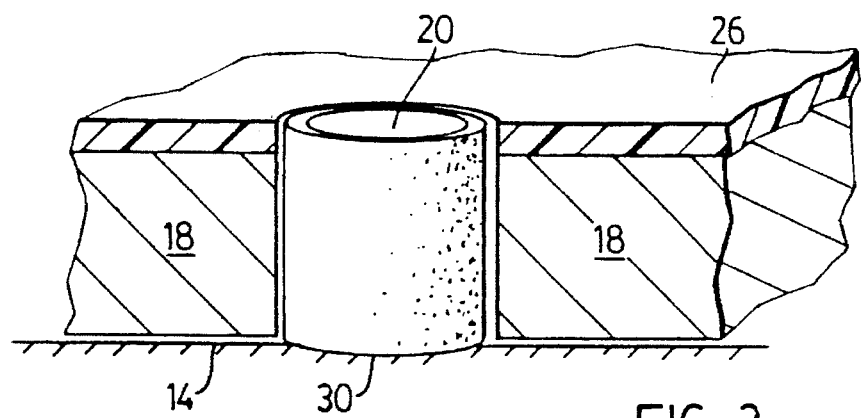
FIG. 2 is a detail of a second preferred, alternative embodiment.

In FIG. 2 of the accompanying drawings, there is shown diagrammatically a detail of a second preferred embodiment of the invention in which the skin compatible adhesive layer 18 is provided with a channel 20 having a liner 30 corresponding to the shape of the channel, preferably but not necessarily constructed of a soft material such as a plastic. A barrier film 26, preferably but not necessarily constructed of a flexible plastic, has an opening in registry with channel 20 and is adherent to skin compatible adhesive layer 18. The liner 30 may be integrally formed with the partitioning upper film 26, which separates the upper surface of the skin compatible adhesive layer 18 from the reservoir 16. The drug composition from a reservoir may thus pass to the underlying skin 14, without contacting the adhesive 18, thereby limiting diffusion of the drug into the adhesive layer 18.

Figure 3:
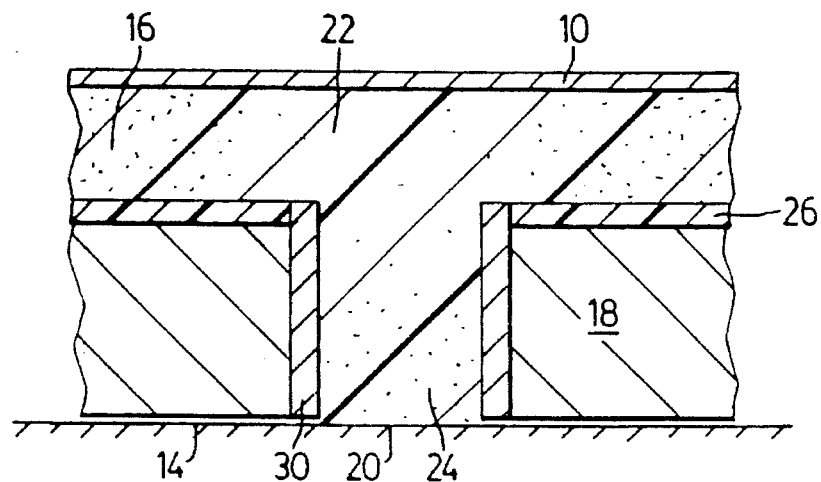
FIG. 3 is a detail of a third preferred, alternative embodiment.

In FIG. 3 of the accompanying drawings, there is shown diagrammatically in cross section a detail of a third preferred embodiment in which the drug reservoir 16 contains a porous support matrix 22 of plastic, foam, etc. acting as a "framework" to hold the liquid drug composition, the reservoir being above partitioning film 26, and the channel 20 is provided with channel liner 30, and contains the same or similar porous support matrix 24.

Figure 4:
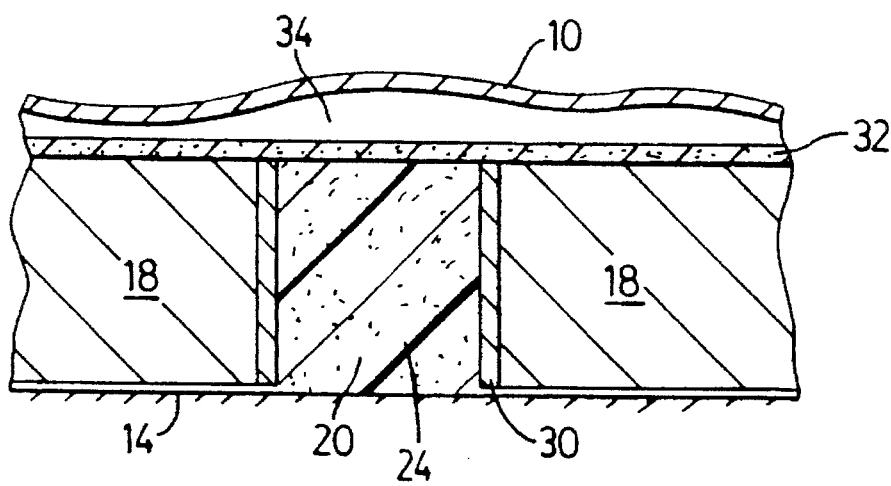
FIG. 4 is a similar detail of a fourth preferred, alternative embodiment.

FIG. 4 of the accompanying drawings similarly illustrates a fragment of a fourth preferred embodiment of the present invention. In this arrangement, the mouth of channel 20 remote from the skin 14 is covered with a porous membrane 32. Channel 20 contains a porous support matrix 24 which contains a network of interconnecting capillaries whose surface characteristics allow effective wetting with a liquid drug composition. The network of interconnecting capillaries provides communication between the skin contacting opening of channel 20 and porous membrane 32. Channel 20 is provided with a channel liner 30, although this can be omitted if appropriate. Porous membrane 32 is preferably chosen to allow passage of only air and solvent vapour and to act as a barrier to liquids which are incompatible with its own surface characteristics. Outer film layer 10 is joined to the remainder of the drug delivery patch at the periphery only, and fits over porous membrane 32 somewhat loosely, so that an air space 34 is created. Porous membrane 32 facilitates the convenient filling of channel 20 from the skin contacting side during manufacture. When a liquid drug composition is brought into contact with the porous support framework 24 in channel 20, the liquid is drawn up by capillary action. Air in the support framework 24 can escape into air space 34 through the porous membrane during the filling process. When drug delivery through skin surface 14 is taking place, the volume of the liquid drug composition may decrease by absorption of some or all of the components thereof. This volume decrease does not create a vacuum within channel 20, because air from space 34 can pass through porous membrane 32 into channel 20. Otherwise, the vacuum created could impede the controlled delivery of the drug.

Figure 5:
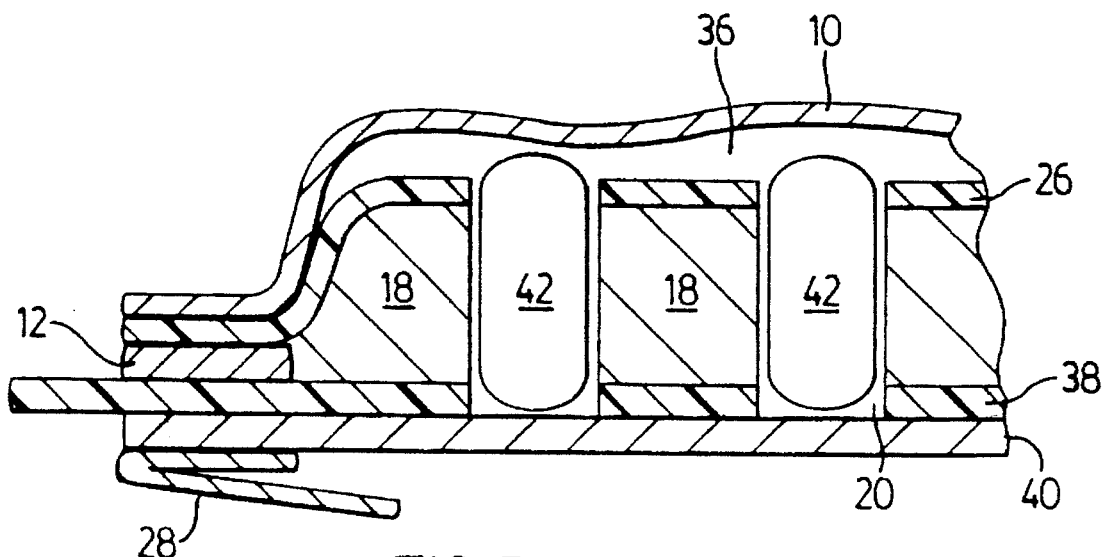
FIG. 5 is a similar detail of a fifth preferred, alternative embodiment of a device but in the form in which it is supplied to a patient before application.

Another, fifth, alternative, preferred embodiment adapted for delivery of a macromolecular drug, is diagrammatically illustrated in FIG. 5 of the accompanying drawings. This embodiment is suitably applied to the patient's skin by procedure described with reference to FIG. 6 below. In one arrangement of the illustrated embodiment of FIG. 5, the channels 20 contain drug delivery bodies 42 which are inert, absorbent bodies such as fibrous pads, free from active drug, but ready to soak up a drug suspension or solution when contacted therewith from the lower end, i.e. via the end adjacent to the inner release liner 38 covering the adhesive 18. In another version of the FIG. 5 arrangement, each channel 20 contains a dry drug delivery body 42 which contains the drug but has no solvent medium. These bodies must be filled with solvent medium just before use by means described below. These bodies constitute reservoirs of soluble therapeutic substance. The provision of the drug in dry form in the body has the major advantage of greatly increased shelf life for those drugs which have poor storage stability in aqueous solution. This is commonly the case for polypeptide drugs, e.g. erythropoietin, whose solutions for injection must be stored at about 5° C. In addition, macromolecular biopharmaceuticals are often very susceptible to microbial degradation. This embodiment also includes an outer film layer 10, an air space 36, a partitioning film 26, a layer of peripherally located adhesive 12 to assist in fixing the patch to the skin, a skin compatible adhesive layer 18, an inner release liner 38 perforated in registry with channels 20 and having a peripherally protruding section, and an outer release liner 40 fitted with tab 28.

The bodies 42 constituting the drug reservoirs in this embodiment can be relatively rigid structures. This is advantageous from a manufacturing point of view, since they can be pushed into appropriately sized holes or channels 20 in the adhesive layer 18 and other structures. Internally, bodies 42 need to have interconnecting, capillary channels extending through them. The surface properties of these capillary channels are preferably such that a drug containing liquid or drug dissolving liquid will be rapidly absorbed on contact. The capillary channels must extend to the projecting extremities of the bodies 42 to permit communication between both sides of the adhesive layer 18. The absorption can take place by the contact of the top or bottom extremities of the bodies 42 with the liquid medium. Communication with the opposite side of the adhesive layer is important to ensure that air in the capillaries of the bodies 42 can be displaced efficiently so that rapid absorption of the fluid can take place. Absorption from the top can be arranged by the provision of a rupturable pouch located in, or in communication with, space 36, said pouch containing a suitable liquid medium, e.g. in the form of a liquid soaked pad, and being rupturable on pressing. Absorption from the bottom, which is especially preferred, is arranged by the device illustrated in FIG. 6, a sixth preferred alternative embodiment of the invention.

Figure 6:
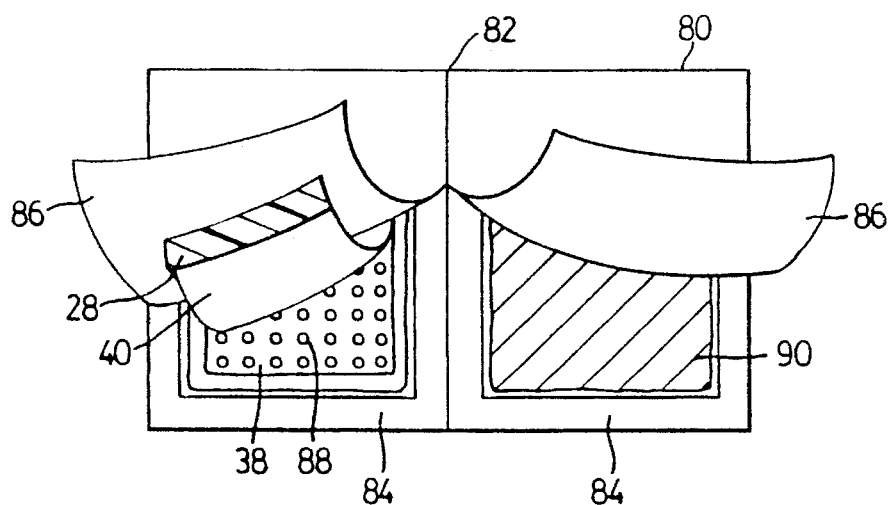
FIG. 6 is a similar detail of a sixth preferred, alternative embodiment of the device, illustrating a preferred system for packaging devices which contain drugs in a solid form.

With reference to FIG. 6, the device generally designated 80 is a system of two lidded pouches, linked along edge 82 in hinged fashion to enable their lidded sides to be folded inwardly on each other. These linked lidded pouches are composed of two relatively stiff pouches 84 and two lids 86 of relatively flexible material. The material used for lids 86 and pouches 84, and the means of removably attaching the lids to the pouches are well known in the art of medical packaging. In the one sealed pouch is a soft support material 90, e.g. fibrous pad, containing a drug dissolving liquid composition, or a drug solution. In the other sealed pouch is a patch of the type illustrated in FIG. 5, with the skin contacting side facing up. Just before the patch is applied to the area of skin to receive transdermally delivered medication, both lids 86 are peeled off. Then outer release liner 40 is removed from the patch by means of tab 28 (FIG. 5). This exposes the surface of the inner release liner 38, in whose perforations are the outwardly protruding ends 88 of bodies 42. The two pouches are then folded inwardly at mutual edge 82 so that the soft, liquid containing support material 90 comes into contact with the surface of inner release liner 38, which is perforated as described above in connection with FIG. 5, and in contact with the outwardly protruding ends 88 of bodies 42. The bodies 42 absorb liquid quickly by capillary action of the fluid in support material 90. During the absorption process displaced air passes into air space 36 shown in FIG. 5. When absorption is complete, the two pouches are folded outwardly, and the patch removed. The inner release liner 38 is then removed by means of the protruding end, thus exposing the skin compatible adhesive 18 and making the patch ready for application to the patient. The dry drug in the bodies 42 is either dissolved therein to provide liquid drug solution for delivery from bodies 42, or, in the alternative case, drug solution is supplied from support material 90 to soak bodies 42.

The form of substance transfer device shown in FIG. 5 is suitable for collection of fluids from a patient's body, for subsequent analysis. Bodies 42 can be removed from the device for analysis, after being in position on the subject's body for the appropriate length of time.

Hyaluronic acid is a preferred macromolecular agent for delivery by use of devices according to the present invention. Hyaluronic acid (HA) is a natural biopolymer found in most animal tissues, with high concentrations found in joints, skin and eyes. Areas of the body under stress, such as arthritic joints, areas of surgical intervention, tumours, wounds etc. tend to become deficient in HA, and when HA is introduced into the body it preferentially accumulates in these depleted areas. HA of appropriate molecular weight is also known to act as a carrier for drugs incorporated therein, (i.e. physically or ionically associated with HA, possibly through envelopment in HA coils, but not covalently bonded). Accordingly, introduction of HA into the body in association with a drug provides a means for targeted delivery of the drug to an area of the body which is under stress, and potentially can benefit from drug therapy.

A wide variety of other therapeutic agents which can be delivered using hyaluronic acid as a carrier and site-director is to be found listed and described in Canadian patent application 2042034 Falk and Asculai, assigned to Norpharmco Inc. and published Mar. 22, 1991. This patent application teaches the combination of HA with low molecular weight drugs, such as furosemide, indomethacin and diclofenac, and with macromolecules such as insulin.

Accordingly, the combination of HA and an associated therapeutic agent incorporated in transdermal drug delivery devices described in the present invention, optionally with suitable adjustment in the molecular weight of the HA, provides an effective means for targeted drug delivery. In addition, HA, even with molecular weight of approximately 500,000 daltons, is apparently able to penetrate intact skin and to carry with it drug incorporated therein. Devices according to the present invention are also useful for delivery of other vector-drug combinations.

It is known that macromolecular polypeptides can be released in a controlled manner from matrices of suitable polymers, most particularly ethylene vinyl acetate (EVA) copolymers. A macromolecular drug, as a dry powder, is incorporated in a polymer matrix in the form of "islands". When the polymer matrix is placed in a suitable aqueous medium, the water diffuses into the polymer and dissolves the macromolecular drug. Osmotic pressure causes the drug to escape from the polymer body, leaving a pore. As long as the islands are close enough to each other, as is the case with high drug loading, interconnected pores form to allow drug from the interior of the polymer matrix to diffuse into the aqueous medium (see R. A. Siegel and R. Langer, Pharmaceutical Research 1, 2 (1984)). More advanced systems, commonly called osmotically rupturable systems, using mixtures of dry electrolyte and dry polypeptide in islands in polymer matrices have been developed by others. One example is a system which has the capability of delivery of polypeptides at a rate which is independent of the polypeptide molecular weight. This was developed by Brian Amsden and Yu-Ling Cheng at the University of Toronto, and was reported in a presentation entitled "The Use of Electrolyte Excipients in the Delivery of Low Loadings of Macromolecular Drugs From EVA Monoliths".

One of the many delivery rate controlling methods which can be employed in the device illustrated in FIG. 5 is the incorporation within body 42 of one or more osmotically rupturable polymer bodies containing the drug to be delivered.

In drug delivery systems of the type to which this invention belongs, it is important to arrange that each specific device for a given treatment purpose has substantially the same total skin contact area of all the drug delivery depots, so that the rate of delivery of a specific drug to a patient's skin does not vary substantially as between specific devices being employed for the same purpose. Otherwise, monitoring and control of the performance of such devices is impractical. In accordance with another aspect of the present invention, there are provided processes for manufacturing transdermal drug delivery devices which result in substantially reproducible total area of skin contact of drug delivery depots, by providing reproducible total area of drug exposure at the bottom surface of the adhesive from device to device. Not only do the manufacturing processes in the present invention accomplish this, but they can also provide a regular array of drug depots exposed at the surface of the skin compatible adhesive layer 18, and can place different depots at specific positions in the array.

Figure 7:
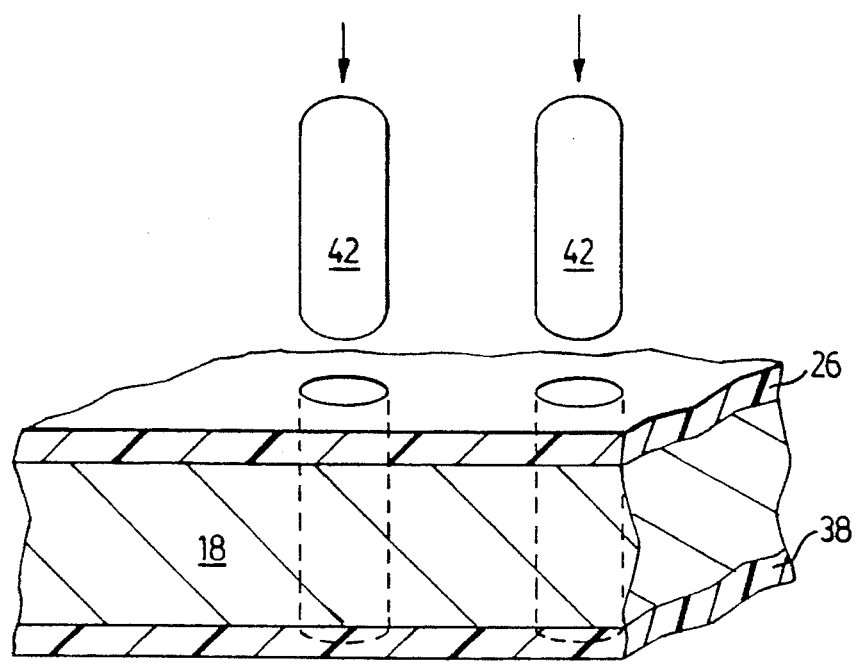
FIGS. 7, 8 and 9 are diagrammatic representations of elements of a manufacturing process for making devices according to preferred embodiments of the invention.
Figure 8:
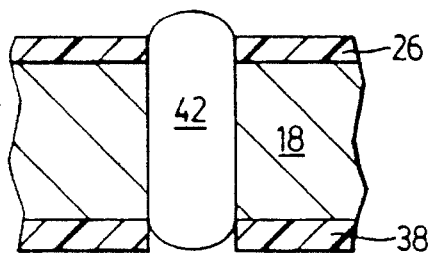

FIG. 7 diagrammatically illustrates a manufacturing method for making drug delivery devices of the type shown in FIG. 5. A layer of skin adhesive 18 sandwiched between top release liner 26 and bottom release liner 38 is perforated with an array of holes such that the perforations extend through release liner 26, adhesive layer 18 and release liner 38. The perforated sandwich is moved to the next manufacturing station in the production line where, in registry with the array of holes, a corresponding array of suitably oriented bodies 42 are pushed into the holes from the side of top release liner 26. The preferred position of body 42 after insertion is illustrated in FIG. 8. This depth on insertion is controlled by the length of the stroke of the mechanical pushing mechanism. Alternatively, a two or more stroke insertion procedure may be adopted, so that the final positioning can be arranged with greater accuracy.

Figure 9:
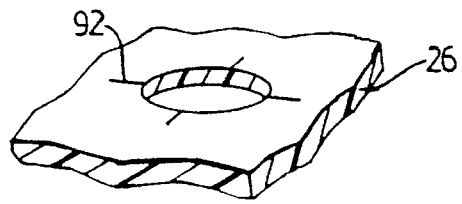

Intimate contact between the outer surfaces of the body 42 and the channel through adhesive layer 18 is preferred. Since skin adhesive 18 is a soft material capable of flow, choice of dimensions of body 42 larger than the receiving dimension of adhesive 18, can be used to ensure intimate contact. Materials contemplated for top release liner 26, however, will not normally be deformed as readily as adhesive 18. Since adhesive 18 and top liner 26 were perforated simultaneously, the choice of dimension of body 42 larger than the receiving dimensions of adhesive 18 will result in dimensions also smaller than the receiving dimensions of the perforations in top liner 26, and consequently a relatively difficult insertion. This problem can be overcome by using a perforating tool which not only effects perforations but also makes slits in the edges of the perforations in the top liner 26. Such perforating tools are known in the art. FIG. 9 illustrates a perforation in top liner 26 which has four slits 92 at the edges. These slits enable the perforation to expand when body 42 of larger cross sectional dimensions is inserted. Slits of this type are especially useful for insertion of bodies which have a spherical shape rather than the "capsule" shape of body 42.

Figure 10:
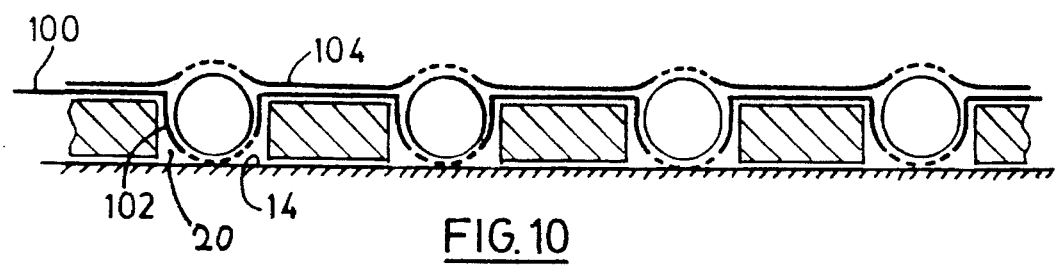
FIG. 10 is a diagrammatic cross-sectional view of a seventh preferred embodiment of the invention.

In FIG. 10 of the accompanying drawings, there is diagrammatically illustrated a seventh preferred embodiment of the invention, resembling that of FIG. 5 in many respects, but offering certain practical advantages in terms of performance and manufacturing simplicity. In common with the other embodiments of the invention, a skin compatible adhesive layer 18 is provided, with channels 20. There is provided a dimpled sheet 100 which extends over the skin-remote surface of the adhesive 18, which contains dimples 102 which protrude into and through the channels 20 in the adhesive layer 18. The dimples 102 contain the drug depots 42, act as liners to separate the depots from the adhesive, and are perforated at the skin contacting side, with a series of apertures of about 0.1 mm in diameter, or by a single larger aperture, to allow drug contact with the underlying skin surface 14. An upper membrane or "cap" sheet 104 is applied over the dimpled sheet 100, to retain the drug depots in position. It is joined to the dimpled sheet 100 at locations where it does not overlie the drug depots 42. It is perforated over the drug depots 42, or otherwise rendered porous, to allow air to pass from and into the top of the body.

Figure 11:
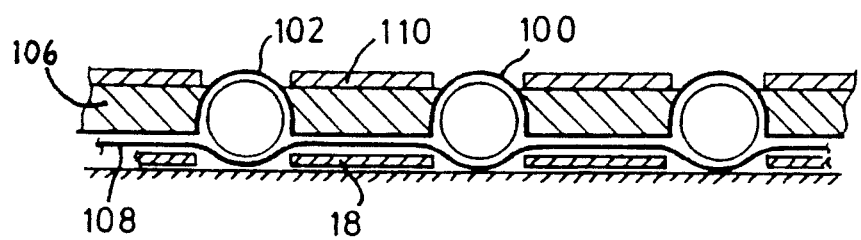
FIG. 11 is a view similar to FIG. 10, but of an eighth preferred embodiment of the invention.

FIG. 11 of the accompanying drawings shows an alternate, eighth preferred embodiment of the invention, resembling that of FIG. 10 in its use of a dimpled sheet 100, to hold and position the drug depots 42. In this embodiment, however, the dimples 102 extend away from the skin surface 14, through an apertured inert filler layer 106, e.g. of plastic foam. A rate-controlling membrane 108, of perforated or semi-permeable skin compatible material, is provided on the skin side of the dimpled sheet 100, and serves to hold the depots 42 in the dimples 102. A layer of skin compatible adhesive 18, perforated in registry with the lower ends of the drug depots 42, is provided on the skin-side surface of the rate controlling membrane 108. The arrangement is completed with a perforated top protective sheet 110, to protect the assembly but also to allow air communication to the drug depots 42.

The embodiments described in connection with FIGS. 10 and 11 utilize the dimpled thermoplastic sheet as a means for holding and locating the drug depots in predetermined array. As noted above, it is preferable to arrange that each specific device for a given treatment purpose has substantially the same total skin contact area of all the drug delivery depots, for predictable drug delivery rates. Manufacturing and assembly advantages of these arrangements according to which this is achieved are apparent from a consideration of their structures. The dimpled sheets may be of any deformable, skin compatible barrier material, such as thermoplastic, thermoset or formable metal such as aluminum.

There is a variety of ways in which dimpled sheets, with the dimples in predetermined array, can be prepared, and many of these are in commercial production. For example, dimpled sheets with a pill sealed in each dimple are widely used in the pharmaceutical industry. They can be created by forming a thermoplastic film at a temperature at which the thermoplastic is soft. They can be vacuum or pressure formed into a mold with depressions. The dimples can be created by placing the material onto a mold, either male or female, and by stamping the material with a suitable die. It can be formed without vacuum forming using male and female counterpart dyes, between which the film is pressed. They can be cold formed.

The perforations in the bottoms of the dimples, which are typically of the order of 0.1 mm in diameter, can be created after the dimples are created in the sheet, or before the dimples are created.

Following formation of the dimples, they are filled with drug depots in the form of a drug solution or suspension, or a capillary network, or solid or semi-solid aliquot of drug in a carrier, or with a matrix containing the drug. Subsequently, the cap sheet 104, for the embodiment of FIG. 10, or the rate controlling membrane 108, for the embodiment of FIG. 11, is applied to the dimpled sheet surface to maintain the drug depots in place within the dimples. Bonding of the sheets at areas away from the drug depots in the dimples can be achieved by use of transfer adhesive, perforated or voided over the depressions to allow free transfer of air, or, in the case of heat sealable sheets of top layer and dimpled lower layer, by application of heat in selected areas which avoid the areas overlying the dimples. The heat sealing process avoids the problems that can be created by contact of an adhesive with the liquid in the drug delivery body. Other methods of joining known in the art, such as ultrasonic welding, can be adopted.

After the drug depots have been inserted into the dimples, and secured therein by application of the cap sheet or rate controlling membrane, the layer of skin compatible adhesive is applied. This is preferably done by application of a perforated sheet of such adhesive, perforated to register with the depressions or dimples in the drug holding assembly. Preferably, the adhesive layer has a release liner on its bottom surface, perforated to register with the dimples, to prevent the bottoms of the drug delivery bodies from striking a lower surface on insertion.

In an alternative arrangement to the FIG. 10 embodiment, the perforated adhesive sheet can be applied to the lower surface of the dimpled barrier sheet before the drug depots are applied thereto, and/or before the cap sheet or membrane is applied to hold the drug depots in place.

Such a device and manufacturing process has a number of advantages. It is well suited for production by commercially proven and viable processes. The "sheets" which are perforated and dimpled can be continuous roll stock. The array of dimples so formed does not have to be continuous. There can be islands of arrays in the roll stock which can be punched out to form individual patches, each such patch having an array of dimples for filling. Moreover, the method and structure provide better tolerance on the position of the bottoms of the drug delivery bodies, with respect to the adhesive. Also, there is a better overall barrier between the drug delivery bodies and the adhesive, and between the adhesive and the top of the patch. The barrier of the top of the patch is particularly important when there is a reservoir above the drug delivery device.

The embodiments described in connection with FIGS. 10 and 11 of the accompanying drawings take advantage of the easy manufacture and availability of dimpled thermoplastic sheets by the pharmaceutical industry for drug packaging purposes. For the present invention, as noted, they provide a most convenient and economical feature of the assemblies, for holding and positioning the drug depots.

Figure 12:
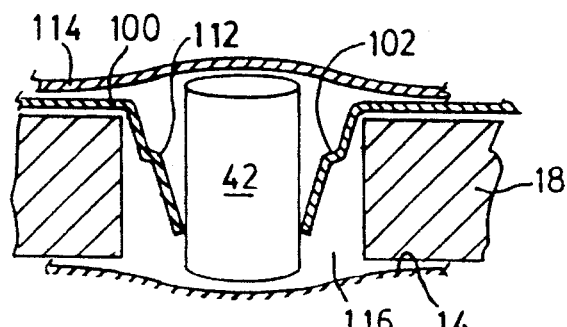
FIG. 12 is a fragmentary diagrammatic cross-sectional view of a ninth preferred embodiment of the invention.

FIG. 12 of the accompanying drawings illustrates diagrammatically a further embodiment utilizing such preformed, dimpled thermoplastic sheets, to hold and position the drug depots, but in which the bottom wall of the dimples have been cut away to provide larger areas of communication between the drug depots and the underlying skin surface 14.

As in the case of all the embodiments of the present invention, that illustrated in FIG. 12 provides direct communication between the drug depot 42 and the skin surface 14 to which the device is applied. The dimpled thermoplastic sheet 100 is pre-cut prior to assembly, to remove the bottoms of the dimples 102 and leave them open ended. This is readily accomplished by passing the sheet over a stationary knife appropriately positioned to achieve the cutting. The side walls 112 are downwardly, inwardly convergent, so that the drug depot 42 is a friction fit therein. The skin compatible adhesive is pre-perforated to register with the dimples of the sheet 100. It is preferably applied as a sheet before insertion of the drug depots 42. A perforated or semi-permeable cap sheet 114 is applied over the drug depots 42 to retain them against upward movement when the device is adhered to press against the skin surface 14. The annular gap 116 thus arranged between the edge of the perforations in the adhesive 18 and the drug depot 14 provides further isolation of the drug delivery body 14 from the edge of the adhesive layer 18.

All of the drug delivery bodies or depots 42 in the device are of substantially uniform size, and project through the skin-side surface of the device to a substantially uniform extent. This can be accomplished by various means used in the insertion process, e.g. by placing the drug delivery bodies 42 in the individual, precut dimples of sheet 100 and then pushing them in to the required depth with a flat plate on a press.

Different shapes and sizes of drug delivery bodies 42 in the embodiment shown in FIG. 12 can be accommodated by changing the shape of the dimple initially formed in the sheet 100. The specific body 42 of FIG. 12 is an elongated cylinder held vertically in the dimpled sheet 110, but in common with other embodiments of the invention has a convex skin-contacting end, for most efficient drug delivery.

The FIG. 12 embodiment is suitable for use as a substance collection device, as well as a drug delivery device.

Figure 13:
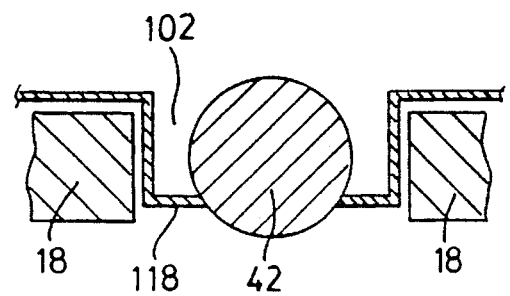
FIG. 13 is a diagrammatic cross-sectional view of a tenth preferred embodiment of the invention.

In FIG. 13 of the accompanying drawings, there is illustrated an embodiment of the invention resembling that of FIG. 12, but in which the bottom wall of the dimple 102 in dimpled sheet 100 has been apertured to provide opposed, inwardly extending lips 118,120 on two edges. The drug delivery depot 42 in this embodiment can be spherical, and is positively retained in position by the lips 118,120. In manufacture, the dimpled sheet 100 is initially formed so that the dimples 102 are shaped to have a main, broad depression and a lowermost nipple depending from the broad depression. The nipple is subsequently cut off, by slicing the continuously moving web with a stationery knife at the desired height, to provide the open ended dimple with lips 118,120 as shown in FIG. 13. The dimples 102 can advantageously be square or rectangular as viewed in plan.

Another preferred shape of drug delivery depot 42 for use in devices according to the present invention, is a disk-shape, i.e. a cylindrical shape in which the diameter of the cylinder exceeds the central axial length, but mounted in the device so that its curved periphery forms the convex, skin-contacting lower end. This can suitably be used also in the embodiment shown in FIG. 13 of the accompanying drawings. The cylindrical axis is thus parallel to the plane of the layer of skin compatible adhesive. Such shapes can be accommodated as friction fits in an open-ended dimple 102, between lips 118 and 120.

Such a short-cylinder or disk-shaped drug delivery depot has a number of practical advantages. Thus it can be conveniently and economically prepared by a simple process of cutting sections from a pre-formed rod of the material, in a transverse direction. Rods of porous materials are relatively easily available, whether in the form of rigid porous plastics or in the form of fibre bundles in the nature of cigarette filters. Such rods can be manufactured with a highly uniform diameter. Moreover, such cylindrical drug delivery bodies, especially when rigid, can be fed to the dimples by a system in which the body is rolled on its circumferential face. The circular cross section allows greater tolerances in the positioning of the drug delivery bodies when they are inserted into the dimples. If the top cross section of the dimple is oversize with respect to the cross section of the drug delivery body perpendicular to the axis of the body, the body can be pushed or rolled into the dimple by relatively simple machinery rather than placed in the dimple by more complex machinery.

Another advantageous shape of drug delivery depot for use in the present invention is a "flattened" cylinder, i.e. a body having an elliptical cross section but with right-angular side walls. These can be mounted in open-bottomed dimple formations as described in connection with FIG. 13 as friction fits additionally held by inwardly protruding lips at the dimple open ends, with convex peripheries extending downwardly towards the patient's skin, for best contact. They can similarly be prepared by cutting from rods of appropriate material. Such shapes offer the advantage that, for a total skin contact area of the drug delivery body, they will depress the skin surface to a lesser degree. Also, for a given total skin contact area, the device as a whole can have a reduced thickness, an important advantage. The embodiment shown in FIG. 13 and the "flattened cylinder" variation, are advantageously manufactured and supplied in the "lidded pouch" form of FIG. 6 so that they can be used with dry-form drugs, made into solution immediately before application.

The FIG. 13 embodiment is suitable for use as a substance collection device, as well as a drug delivery device.

Figure 14:
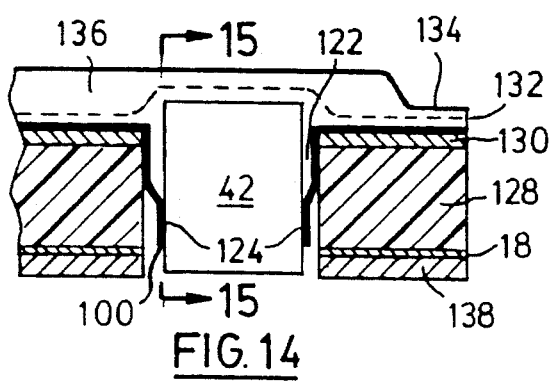
FIGS. 14 and 15 are diagrammatic cross-sectional illustrations of an eleventh and most preferred embodiment of the present invention, taken at right angles to one another.
Figure 15:
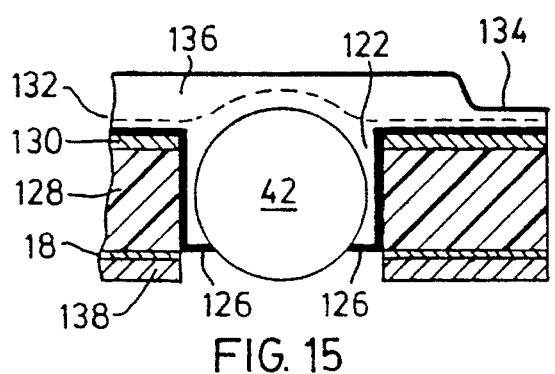

The embodiment of the invention illustrated in FIGS. 14 and 15 is similar in many respects to that shown in FIGS. 12 and 13, in that it utilizes a dimpled sheet 100 of thermo formed material from which the bottoms of the dimples have been cut to provide lipped apertures through which the drug depot 42 can protrude and in which it is held and positioned. The drug depot is cylindrical in shape, elongated along its cylindrical axis so that its axial length is its longest dimension. It is held in the well 122 formed by cutting off the bottoms of the preformed dimples, with its cylindrical surface protruding downwardly for skin contact. Its flat side faces are held between inwardly protruding opposed flat sidewalls 124 of the well 122, as shown in FIG. 14, whilst its cylindrical face rests on inwardly protruding opposed lips 126 of the well 122, as shown in FIG. 15, which is a view at right angle to that of FIG. 14.

The bulk of the thickness of the patch of this embodiment is comprised of a layer of inert, closed cell plastic foam 128, apertured to form the wells 122, and to the top surface of which is adhesively attached, by means of an adhesive layer 130, the thermo formed sheet 100 in which the dimples are thermoformed and then cut as described. A porous securing sheet 132 overlies the thermoformed film 100 and the drug depots 42 in the wells 122, and a barrier layer 134 is sealed, at areas remote from the wells 122, to the upper surface of the securing sheet 132, leaving air spaces 136 above the drug depots 42 to facilitate drug delivery therefrom.

The skin compatible adhesive 18 for this embodiment is provided as a thin layer on the bottom surface of the foam layer 128, perforated in registry with wells 122 therein, and protected on its lowermost surface by a release sheet 138 which is removed prior to application of the patch to the skin. The provision of the skin compatible adhesive 18 as a thin layer, as in this embodiment, has the distinct advantage of significantly improving the dimensional stability of the patch as a whole, when exposed to moisture. Many of the acceptable skin compatible adhesives useful in the patches according to the present invention are hydrophilic, and absorb moisture, whereupon they expand. This can cause separation of the drug depots from the patient's skin if too great an expansion takes place. The thinner the layer of skin compatible adhesive, the smaller the amount of such expansion, and the greater the dimensional stability of the patch as a whole.

The FIGS. 14 and 15 embodiment is useful as a substance collection device, as well as a drug delivery device.

This embodiment of the invention is also useful in iontophoretic drug delivery systems, where an electrode is placed in contact with the drug depots 42, and the patient also wears an appropriate electrical grounding pad.

The embodiment of the invention shown in FIGS. 14 and 15 also has the advantage of manufacturing ease. The shapes of the drug depots allow them to be applied to the dimpled, cut, thermoformed sheet 100 by dropping them onto the surface, since they will naturally fall on their cylindrical surfaces, and roll across the sheet surface to enter the wells 122 in the desired orientation. The shapes of the side walls and lips of the wells 122 are easily formed and cut to provide positive gripping and predetermined positioning of the drug depots as required. The manufacturing and assembly process for the patches of this embodiment can be operated continuously and rapidly, as described below in connection with FIGS. 18–20.

The drug delivery bodies used in these "dimpled sheet" embodiments can be formed from many materials and can have many different internal structures. They can for example be porous bodies which are relatively easily compressed. Such a body may be compressed in use in a transdermal drug delivery device by pressure applied to the top or air side of the device, especially when the body protrudes above the level of the dimpled sheet. When the compressible, porous drug delivery body contains a fluid, the compression will act to create hydraulic pressure. An advantage of the combination of a dimple shape and a drug delivery body shape which creates an air space between the inside of the dimple and the outside of the drug delivery body is that the hydraulic pressure can be dissipated by the flow of the liquid into this air space. This tends to counteract any tendency of the hydraulic pressure to disrupt the adhesion of the transdermal device to the skin. When the pressure on the compressible drug delivery body is relieved, it will recover some or all of its original shape, and in so doing, it absorbs some of the liquid expressed into the air space. The relief of hydraulic pressure is even more effectively facilitated if the securing layer which covers the tops of the drug delivery bodies (the side remote from the skin) and holds them in place is perforated to allow the egress and ingress of air.

Figure 16:
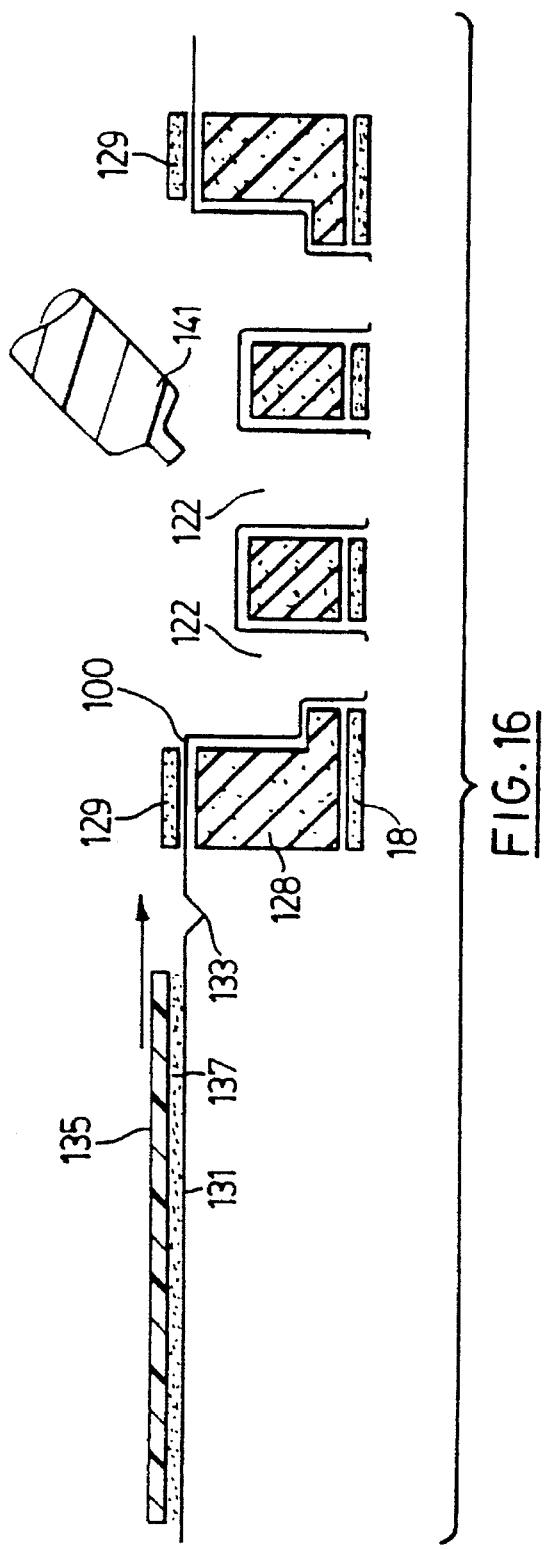
FIGS. 16 and 17 are diagrammatic cross-sectional illustrations of another, twelfth embodiment of the invention, especially for use with semi-solid, freshly prepared drug formulations.
Figure 17:
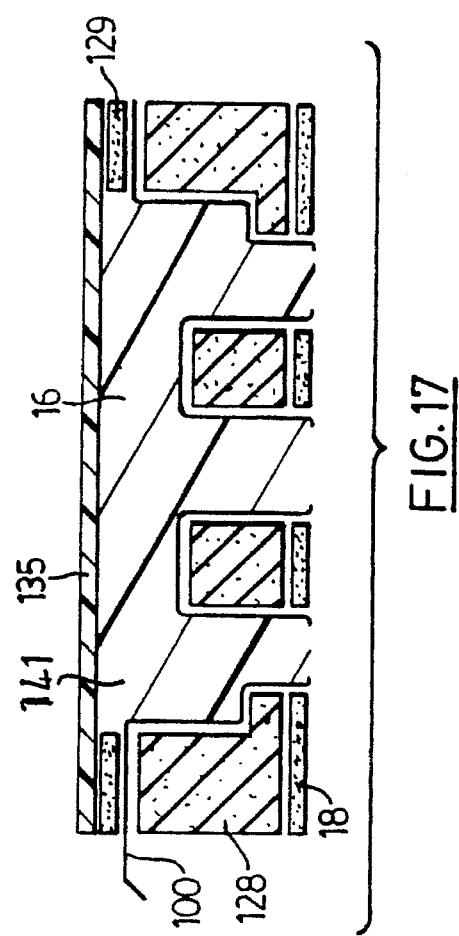

The embodiment of the invention illustrated in FIGS. 16 and 17 is especially useful for administering semi-solid drug formulations which are prepared immediately prior to application of the device to the patient.

Structural items of this embodiment are similar in many respects to those of the FIGS. 14 and 15 embodiment. Thus a dimpled, cut, thermoformed sheet 100 is used, to form lined channels for drug delivery. The dimples are surrounded by a layer of inert, closed cell plastic foam 128 appropriately apertured to form the wells 122. At its periphery, the plastic foam structures 128 rise above the top extremities of the internal structures, to form an upper reservoir 16. The sheet 100 is adhesively attached to the foam layer 128. The inner, bottom surface of the foam layer 128 carries the layer of body contacting adhesive 18. The peripheral rim of the sheet 100 is provided on its upper surface with adhesive 129.

The sheet 100 is provided with a lateral extension 131, joined to the rest of the sheet 100 by means of a weakened hinge 133. The upper surface of extension 131 carries a lid 135 adhered thereto by weak adhesive 137.

In the open position illustrated in FIG. 16, before or after application of the device to the patient, the wells 122 are filled to overflowing with a freshly prepared, semi-solid drug formulation 141, e.g. from a spreader nozzle. Then the lateral extension 131 is hinged about weakened hinge 133 to bring the lid 135 into contact with adhesive 129. The lateral extension 131 is peeled off the lid 135 and broken away at weakened hinge 133. Now the device has the appearance shown diagrammatically in Fig. 17. The upper space defined by the lid 135 and the raised periphery of the device effectively forms an upper reservoir 16 containing semi-solid drug formulation 141, which also extends into the wells or channels 122 and from these can contact the patient's skin after adhesive application of the device to the skin using adhesive 18.

The manufacturing process for the embodiment of the invention illustrated in FIGS. 14 and 15 is diagrammatically presented in FIGS. 18, 19 and 20. It comprises three co-operative assembly lines. The first, the subject of FIG. 18, starts with a roll 140 of the closed cell foam material 128, and a roll 142 of the laminate of the skin compatible adhesive 18 and its protective release liner 138. These are laminated together at a first station between nip rollers 144, and then proceed on a supporting conveyor 145, to a second station 146 where the laminate is punched in a predetermined pattern to form groups of apertures to serve as wells for the eventual reception of the drug delivery depots. Typically, the wells are formed in groups of twelve, to provide patches having twelve depots. The top view of the laminate as it appears at each station is diagrammatically shown below the assembly line in FIG. 18.

Next, at station 148, the laminate is die cut to form individual patches 150 with the apertures punched therethrough, and the residual roll of laminate is led away at station 152 by a strip ladder. Then the individual patches 150 supported on the conveyor 145 are laminated to the product of the second assembly line shown in FIG. 19, which approaches in the transverse direction with respect to the direction of travel of the conveyor 145 of FIG. 18.

The assembly line of FIG. 19 starts with a roll 154 of thermoformable plastic sheet 100. This is continuously unrolled and, at station 156, is thermoformed to create dimples therein, of predetermined, precise shape and size. At the next station 158, these are cut to provide the required lips 126 and sidewalls 124 (not shown). Next, at station 160, the cylindrical drug depots 42 are dropped into the open-bottomed dimples, to assume the position and orientation described in connection with FIG. 13. At station 162, the porous securing sheet 132 is applied and appropriately heat sealed to the sheet 100 as previously described. The assembly then encounters at station 164 the laminated patches 150 from the production line of FIG. 18, approaching in the transverse direction at a synchronised speed and in appropriate registry. The laminated patches 150 from FIG. 18 are applied to the underside of the assembly of FIG. 19 so that a drug depot 42 protrudes into and is held in each well. Then at the next station 166 barrier layer 134 is applied and heat sealed in position. Subsequently, the product is die cut at station 168 to the required shape and size.

The third assembly line shown in FIG. 20 starts with a roll 170 of thermoplastic barrier film to form part of the eventual hermetic sealing arrangement of the final product. The barrier film 172 is thermoformed or cold formed into blisters 174, each of which receives at station 176 a patch 150 from the previously described assembly lines. At the next station 178 liquid drug solution is applied to the drug depots 42, and then, at station 180, a barrier film layer 182 is heat sealed or otherwise sealed to barrier layer 174, to complete the hermetic sealing of the patches 150. The product is then die cut to its final size and shape at station 184 and led away for cartoning.

The invention is further illustrated in the following specific examples.

EXAMPLE 1

IN VITRO TRANSDERMAL DELIVERY USING A DEVICE ACCORDING TO FIG. 2

The skin penetration of model compounds from a transdermal patch constructed according to FIG. 2 was established in vitro by a permeation study. A circular adhesive layer 3.5 cm in diameter and 0.3 mm thick of the polyethylene oxide/polyacrylic acid adhesive disclosed in U.S. Pat. No. 4,920,158 Murray et al. was perforated with an array of 69 cylindrical channels approximately 1.24 mm in diameter. The array measured 1.7×1.7 cm and was centrally located. These channels were lined with sections of silicone tubing (Silastic Medical Grade, No. 602-155, Dow Corning) such that each tubing section was approximately even with the bottom, skin contacting side of the adhesive layer, but protruded slightly above the top or outer side. On this outer surface of the adhesive layer, but between the slightly protruding silicone tubing was cast a 30% solution of silicone sealant in hexane. The channels were filled with filaments of open cell polyurethane foam. On top of the dry silicone layer was placed a reservoir support layer consisting of a 1.5 mm thick sheet of the same open-cell polyurethane foam, 2.0 cm in diameter. The outer, barrier layer of the patch was a 3.5 cm diameter section of DERMAFLEX V-300-F FLESH (vinyl coated with a medical grade acrylic adhesive, FLEXCON Company). The reservoir and channels of the patch were loaded with a solution which contained a fluorescently labelled model compound (polypeptides or polysaccharide). The test apparatus (Model LG-1082, Laboratory Glass Apparatus, Inc. Berkeley, Calif.) consisted of a series of glass diffusion cells maintained at 37° C. The sections of modified skin (stratum corneum removed) were excised from the Hairless Guinea Pig and mounted on the diffusion cell above a solution of isotonic saline such that the dermal side of skin was in contact with the magnetically stirred receptor liquid. The device was brought into intimate contact with the epidermal surface of the skin. The effective contact area of the solution with the skin through the channels was 0.21 cm$^2$. In general terms, the reservoir solution, at the start of the experiment, contained about 1 mg of model compound. Duplicate samples of each test compound were run. The amount of the labelled compound which diffused from the patch to the receptor solution during the study was measured using a SLM-4800S Spectrofluorimeter and representative data is shown in Table 1. Less than ideal intimate contact between the adhesive and the epidermal surface of the skin was achieved throughout the period of the testing, largely due to the compromised, incomplete nature of the epidermal surface.

TABLE 1

Permeation of Model Compounds Through the Skin

| Patch Label | Compound (Molecular Weight In Daltons) | Amount Permeated in 20 Hrs. (Micrograms) |
| --- | --- | --- |
| PYQ-TS-C-86 | Insulin (polypeptide, 5,500) | 0.04 |
| PYQ-TS-C-87 | | 0.05 |
| PYQ-TS-C-90 | Casein (polypeptide, 23,000) | 0.05 |
| PYQ-TS-C-91 | | 0.03 |
| PYQ-TS-C-76 | Dextran (polysaccharide, 9,400) | 1.22 |
| PYQ-TS-C-77 | | 2.61 |
| PYQ-TS-C-53 | Dextran (polysaccharide, 71,200) | 0.71 |
| PYQ-TS-C-54 | | 0.53 |

EXAMPLE 2

IN VITRO TRANSDERMAL DELIVERY USING A DEVICE ACCORDING TO FIG. 2

The skin penetration of fluorescently labelled model compounds from a transdermal patch constructed according to FIG. 2 was established in vitro by a permeation study similar to Example 1, again using compromised skin, except that:

The skin compatible adhesive comprised laminated layers of Dermaflex V-300—CM H566 (FLEXCON Company, Inc.), 0.3 mm thick, perforated with an array of 69 cylindrical channels approximately 1.24 mm in diameter.

Intimate contact of the patch with the skin was maintained throughout the test. The initial loading of the drug solution reservoir was in each case approximately 1 mg. Duplicate experiments were conducted in each case.

The amount of the labelled compound which diffused from the patch to the receptor solution during the studies is shown in Table 2.

TABLE 2

Permeation of Model Compounds through the Skin

| Patch Label | Compound (Molecular Weight in Daltons) | Amount Permeated in 20 Hrs. (Micrograms) |
| --- | --- | --- |
| PYQ-TS-C-107 | Insulin (polypeptide, 5,500) | 10.85 |
| PYQ-TS-C-108 | | 8.30 |
| PYQ-TS-C-115 | Dextran (polysaccharide, 9,400) | 66.28 |
| PYQ-TS-C-116 | | 64.50 |

EXAMPLE 3

IN VIVO TRANSDERMAL DELIVERY USING A DEVICE ACCORDING TO FIG. 2

The skin penetration of a radioactive carbon-14 labelled Dextran (a polysaccharide of molecular weight 10,000 Daltons) from a transdermal patch constructed according to FIG. 2 was established by an in vivo study using four female Hairless Guinea Pigs.

The patch devices used in the in vivo study were the same as described in Example 2. The stratum corneum of three animals was compromised over a 3×3 cm area in a dorsal lateral location. A transdermal patch was applied to the comprised skin site. A transdermal patch was also applied to a fourth animal to the same area on intact skin. Blood and urine samples were removed from each of the four animals at 1 day. The amount of carbon-14 Dextran which diffused from the patch to the animal was measured using the urine and blood samples collected. A single channel carbon-14 liquid scintillation counter (LKB Wallac, Model #1215) was used for the quantitation of carbon-14 activity. Results from the in vivo study is shown in Table 3.

TABLE 3

In vivo Permeation of Carbon-14 Dextran
(Molecular Weight of 10,000 Daltons) Through Hairless Guinea Pig

| Animal # | Skin Preparation | Level of Activity in the Urine | | Level of Activity in the Plasma | |
|---|---|---|---|---|---|
| | | Becquerels/g | Micrograms/g* | Becquerels/g | Micrograms/g* |
| 112 | Compromised | 198 | 2.7 | 15.9 | 0.21 |
| 113 | Compromised | 149 | 2.0 | — | — |
| 118 | Compromised | 148 | 2.0 | 12.8 | 0.17 |
| 117 | Intact | 14 | 0.2 | 0.8 | 0.01 |

*equivalent concentration of Carbon-14 Dextran

EXAMPLE 4

IN VITRO TRANSDERMAL DELIVERY USING A DEVICE ACCORDING TO FIG. 3

The skin penetration of fluorescently labelled model compounds from a transdermal patch constructed according to FIG. 3 was established in vitro by a permeation study similar to Example 1, except that:

skin compatible adhesive, H-566 coated onto a white polyethylene closed cell foam, 0.8 mm thick (Dermaflex PEF 32-W H-566 from Flexcon Company, Inc.) was used, perforated with an array of 69 cylindrical channels approximately 0.84 mm in diameter;

the channels were not lined; instead they were filled with cylindrical sections of porous plastic material (Hydrophilic HDPE with medium pore size, NO. X-4899, Porex Technologies);

the silicone sealant was absent; a reservoir support layer consisting of 1.6 mm thick sheet of porous plastic material, 2.0 cm in diameter (Hydrophilic HDPE with coarse pore size, NO. X-4916, Porex Technologies) was placed directly above the array of 69 channels;

the effective contact area of the model compound solution with the skin through the porous plastic depots was 0.35 cm².

The amount of labelled compound which diffused from the patch to the receptor solution during the studies is shown in Table 4. Some variability in results, as between attempted duplicates, was observed, largely attributable to uncertain intimate contact between the reservoir and the skin contacting matrices.

TABLE 4

Permeation of Model Compounds Through the Skin

| Patch Label | Compound (Molecular Weight in Daltons) | Amount Permeated in 20 Hrs. (Micrograms) |
|---|---|---|
| PYQ-TS-E-11 | Insulin (polypeptide, 5,500) | 41.96 |
| PYQ-TS-E-13 | | 22.78 |
| PYQ-TS-E-19 | Casein (polypeptide, 23,000) | 75.98 |
| PYQ-TS-E-20 | | 104.98 |
| PYQ-TS-E-28 | Dextran (polysaccharide, 71,200) | 12.28 |
| PYQ-TS-E-29 | | 13.00 |

EXAMPLE 5

IN VITRO TRANSDERMAL DELIVERY USING A DEVICE ACCORDING TO FIG. 14 and 15

The skin penetration of model compounds from a transdermal patch constructed according to FIGS. 14 and 15 was established in vitro by a permeation study. The device was comprised of a circular layer of white polyethylene closed cell foam coated with a skin-contacting H-566 adhesive (total thickness 1.6 mm, Dermaflex PEF-16-W H-566 from Flexcon Company, Inc.) which was perforated with an array of 12 rectangular channels, approximately 3×4 cm in size. The array of rectangular channels measured 1.9×2.2 cm and was centrally located. A thermoformable polypropylene sheet, (10 ml thick, #PP9234 from Rexene Products) in which a similar array of 12 dimples had been formed and the bottom most portions of the dimples had been cut away to provide lips as shown at 126 on FIG. 15, of extent about 0.5 mm, was secured to the uppermost surface of the closed cell polyethylene foam by means of a layer of perforated transfer adhesive (Cotran #9872 PGTA from 3M Pharmaceuticals). The wells were filled with porous plastic. The porous plastic depots, measured 3 mm in length and were cut from an UHMW polyethylene rod, 3 mm in diameter (Hydrophilic, No. X-5552 from Porex Technologies). A porous securing sheet (CoTran #9710 microporous polyethylene film from 3M Pharmaceuticals) or a suitable perforated plastic sheet, typically found in Curad TELFA pads (Kendall Canada) was secured onto the thermo formed film by means of a second layer of perforated transfer adhesive. A barrier layer of polyethylene film, 2.5 cm in diameter (2-HID-ST81B-WHT, Release Technologies) was sealed to the under surface of the outer top sheet of the patch, a 3.5 cm diameter section of dermaFlex V-300-F-FLESH (Flexcon Company Inc.), leaving air space above the drug depots to facilitate drug delivery. The depots were loaded with a solution (liquid reservoir system) which contained a radioactive carbon-14 labelled model compound. The test apparatus and Hairless Guinea Pig skin preparation were the same as Example 1. The effective contact area of the model compound solution with the skin was 1.1 cm². The amount of carbon-14 labelled compound which diffused from the patch to the receptor solution during the study was measured using a single channel carbon-14 liquid scintillation counter (LKB Wallac, Model #1215). Representative data is shown in Table 5.

TABLE 5

Permeation of Model Compounds Through the Skin

Amount Permeated

| Patch Label | Compound (Molecular Weight In Daltons) | Hrs | (Cumulated micrograms) |
|---|---|---|---|
| PYQ-TS-F-35 | Dextran (polysaccharide 10,000) | 8 | 109.1 |
| | | 24 | 289.6 |
| | | 48 | 463.2 |
| PYQ-TS-F-36 | | 8 | 87.0 |
| | | 24 | 246.3 |
| | | 48 | 428.2 |
| PYQ-TS-F-60 | Cytochrome C* (polypeptide, 12,300) | 4 | 117.8 |
| | | 8 | 257.5 |
| | | 24 | 581.6 |
| | | 48 | 740.0 |
| PYQ-TS-F-61 | | 4 | 103.4 |
| | | 8 | 239.8 |
| | | 24 | 572.6 |
| | | 48 | 728.3 |

*from horse heart

EXAMPLE 6

IN VITRO TRANSDERMAL DELIVERY USING DEVICE ACCORDING TO FIGS. 14 AND 15 INVOLVING INTACT SKIN

The skin penetration of carbon-14 labelled estradiol (an estrogen with a molecular weight of 272 Daltons) from a transdermal patch was established in vitro by a permeation study similar to Example 5, except that the stratum corneum of the Hairless Guinea Pig was not removed. In addition to the transdermal patches using porous plastic depots as described in Example 5, patches containing fibrous depots were also tested. The fibrous depots, also measured 3 mm in length were cut from an aligned bonded cellulose acetate rod, 3 mm in diameter (R14236 from American Filtrona Co.).

Data from the permeation of estradiol is shown in Table 6.

TABLE 6

Permeation of Estradiol Through Intact Skin

| Patch Label | Matrix Compositions | Hrs | Amount Permeated (Cumulative Micrograms) |
|---|---|---|---|
| PYQ-TS-F-41 | Fibrous | 8 | 0.19 |
| | | 24 | 1.74 |
| | | 48 | 2.99 |
| PYQ-TS-F-42 | Fibrous | 8 | 0.34 |
| | | 24 | 2.93 |
| | | 48 | 4.83 |
| PYQ-TS-F-44 | Porous Plastic | 8 | 1.01 |
| | | 24 | 6.14 |
| | | 48 | 9.90 |
| PYQ-TS-F-45 | Porous Plastic | 8 | 1.03 |
| | | 24 | 6.87 |
| | | 48 | 10.69 |

EXAMPLE 7

IN VITRO TRANSDERMAL DELIVERY USING A DEVICE ACCORDING TO FIGS. 14 AND 15 INVOLVING A DRIED DRUG MATRIX

The skin penetration of carbon-14 labelled model compounds from a transdermal patch constructed according to FIGS. 14 and 15 was established in vitro by a permeation study similar to Example 5 except that porous plastic or fibrous depots were loaded with a model compound solution, and freeze dried before they were placed into the wells of the patch (solid reservoir system). The drug depots were hydrated with a suitable solubilizing solution just before the start of the permeation study, as illustrated in FIG. 6. Representative data is shown in Table 7.

TABLE 7

| Patch Labels | Compound (Molecular Weight In Daltons) | Matrix Composition | Hrs | Amount Permeated (Cumulative Micrograms) |
|---|---|---|---|---|
| PYQ-TS-F-31 | Dextran (polysaccharide, 10,000) | Fibrous | 8 | 22.2 |
| | | | 24 | 121.2 |
| | | | 48 | 300.0 |
| PYQ-TS-F-32 | | | 8 | 50.8 |
| | | | 24 | 305.5 |
| | | | 48 | 654.0 |
| PYQ-TS-F-33 | Dextran (polysaccharide 10,000) | Porous Plastic | 8 | 68.1 |
| | | | 24 | 223.3 |
| | | | 48 | 382.5 |
| PYQ-TS-F-34 | | | 8 | 58.3 |
| | | | 24 | 179.6 |
| | | | 48 | 279.1 |
| PYQ-TS-F-58 | Cytochrome C* (polypeptide 12,300) | Porous Plastic | 4 | 40.4 |
| | | | 8 | 124.2 |
| | | | 24 | 412.6 |
| | | | 48 | 642.7 |
| PYQ-TS-F-59 | | | 4 | 40.4 |
| | | | 8 | 119.9 |
| | | | 24 | 363.1 |
| | | | 48 | 560.6 |

*from horse heart

EXAMPLE 8

IN VITRO TRANSDERMAL DELIVERY USING A DEVICE ACCORDING TO FIGS. 14 AND 15 AND A COMMERCIAL IONTOPHORESIS POWER SUPPLY

Iontophoretically assisted skin penetration by Dexamethasone Sodium Phosphate delivered by a transdermal patch of the form shown in FIGS. 14 and 15 was established in vitro by a permeation study.

In order to accommodate both the grounding pad and the drug patch on the same section of skin, a larger diffusion cell, but one of the same type as described in Example 1 was used. A piece of closed cell polyethylene foam (Dermaflex PEF-16 white with H-566 skin contacting adhesive, from Flexcon Company, Inc.) was adhered to the skin. The foam had two compartments cut out in a manner such that, when the grounding pad and the drug patch were adhered to the skin, they were separated by a 6 mm strip of the polyethylene foam.

In one compartment of the polyethylene foam, there was applied a dispersive pad, connected to the positive electrode lead (TL2-Twin Lead from Iomed, Inc.). To the second, slightly larger compartment in the polyethylene foam, there was applied a modified transdermal patch. This patch consisted of a layer of white polyethylene closed cell foam, a thermoformable polypropylene sheet with 12 dimples each filled with a porous plastic depot, as described in Example 5. These 12 porous plastic depots were wetted with Dexamethasone Sodium Phosphate solution. A Trans Q1 or Trans Q2 drug reservoir pad, was also wetted with the same Dexamethasone Sodium Phosphate solution and placed on top of the transdermal patch containing the 12 porous plastic depots. As compared with the device illustrated in FIGS. 14 and 15, items 130 and 132 had effectively been replaced with the wettable drug pad of the iontophoretic unit. A section of an outer barrier layer (Dermaflex V-300-CM with H-566 adhesive, from Flexcon Company, Inc.), was placed on top of the Trans Q1 or Trans Q2 reservoir pad and secured to the polyethylene foam surrounding the compartment so that the Trans Q1 or Trans Q2 reservoir pad was in intimate contact with the transdermal patch beneath it. The Trans Q1 or Trans Q2 reservoir pad was then connected to the negative electrode lead. The two electrode leads were connected to a power supply (Phoresor PM 600, from Iomed Inc.). A current of 4 mA was used and the assembly (PTQ-TS-F-95) was in contact with the skin (stratum corneum intact) for 40 minutes.

The amount of Dexamethasone Sodium Phosphate detected in the receptor solution, as analyzed by HPLC, was 7.63 μg.

In a separate experiment, using a similar assembly of components, reference PYQ-TS-F-92, the device was in contact with the skin (stratum corneum intact) for a period of current administration of 120 minutes. In this experiment, the amount of Dexamethasone Sodium Phosphate detected in the receptor solution was 21.89 μg.

In yet another, separate experiment, a similar patch system assembly was placed in contact with skin which had the stratum corneum removed, only in the area where it was in contact with the transdermal patch. The amounts of Dexamethasone Sodium Phosphate detected in the receptor solution at the end of 40 minutes (Experiment PYQ-TS-F-96) at 120 minutes (Experiment PYQ-TS-F-93) were 8.44 μg and 71.85 μg respectively.

EXAMPLE 9

IN VITRO TRANSDERMAL DELIVERY USING A DEVICE ACCORDING TO FIGS. 14 AND 15, INVOLVING A SKIN PENETRATION ENHANCER

Skin penetration of Indapamide from a transdermal patch constructed according to FIGS. 14 and 15 was established in vitro by a permeation study similar to that described in Example 5. The 12 dimples in the sheet were filled with porous plastic depots, to which was added an Indapamide solution. A separate patch was loaded with a similar Indapamide solution but also including the penetration enhancer AZONE (1-dodecylhexahydro-2H-azepin-2-one). The transdermal patches containing the two different drug formulations were tested using both intact and compromised (stratum corneum removed) Hairless Guinea Pig skin. The amount of Indapamide present in the receptor solution was analyzed by HPLC. Data from the permeation of the two drug formulations from the transdermal drug patch is shown in Table 8.

TABLE 8

Permeation of Indapamide Through the Skin

| Patch Label | Skin Preparation | Penetration Enhancer | Amount Permeated in 16 Hrs. (Micrograms) |
| --- | --- | --- | --- |
| PYQ-TS-F-104 | Intact | None | 3.9 |
| PYQ-TS-F-105 | Intact | None | 0.8 |
| PYQ-TS-F-102 | Intact | Azone | 283.8 |
| PYQ-TS-F-103 | Intact | Azone | 342.9 |
| PYQ-TS-F-106 | Compromised | None | 726.5 |
| PYQ-TS-F-107 | Compromised | None | 715.7 |

We claim:

1. A topically applicable substance transfer device for transdermal or topical transfer of substances to and from a living body, said device having an inner surface for body contact, and further comprising:

a layer of skin compatible adhesive having an inner surface for body contact;

a plurality of channels extending through the layer of adhesive, each said channel having an inner opening at the inner surface of the device substantially completely surrounded by adhesive;

substance depots in liquid communication with the inner openings of at least some of said channels and adapted to transfer substance to and from said openings, said substance depots having inner surfaces which protrude beyond the inner surface of the adhesive layer;

said inner surface of the device being comprised of discrete areas constituted respectively by the inner openings of said channels and by the inner surface of said adhesive layer;

and said channels being lined with barrier material to impede diffusion between the substance depots and the adhesive.

2. The transfer device according to claim 1, wherein said substance depots contain topically or transdermally administratable drug.

3. The transfer device according to claim 2, wherein said substance depots comprise liquid or semi-solid drug formulation.

4. The device according to claim 3, wherein said substance depots comprise reservoirs of liquid drug solution disposed within the channels.

5. The device according to claim 4, wherein said reservoirs of liquid drug solution include solid particles of undissolved drug.

6. The device according to claim 4, wherein the reservoirs comprise porous matrix supports for the drug solution.

7. The device according to claim 6, wherein said porous matrix supports comprise open cell foam, pad, fibrous mat or porous plastic bodies supporting the drug solution.

8. The device according to claim 4, wherein said reservoirs comprise liquid drug encapsulated in a semi-permeable membrane.

9. The device according to claim 2, further including a layer of barrier material covering the outer surface of the layer of skin compatible adhesive material to impede diffusion of drug into the adhesive material.

10. The device of claim 9, wherein the layer of barrier material is integral with the barrier material lining said channels.

11. The device according to claim 2, wherein said substance depot comprises dry drug formulation.

12. The device according to claim 11 further including a means for applying drug delivery fluid to the dry form drug immediately prior to application thereof to the body surface.

13. The device according to claim 12, wherein the drug is present in the channels as discrete depots, with lower surfaces of said depots exposed at the inner surface of the skin compatible adhesive layer.

14. The device according to claim 13, wherein the exposed lower surfaces of the drug depots are convexly curved in the downward direction.

15. The device of claim 10, wherein the integral layer of barrier material and barrier material lining said channels comprises a dimpled barrier sheet having a planar portion overlying the outer surface of the skin compatible adhesive layer, the dimples therein protruding towards the inner surface of the adhesive layer and lining said channels, the inner ends of said dimples having apertures to provide communication between the substance depot and the inner surface opening through said adhesive layer.

16. The device of claim 15, wherein said apertures comprise a plurality of perforations therethrough.

17. The device of claim 15, wherein each said dimple has a single aperture therethrough.

18. The device of claim 17, wherein the side walls of each said dimple are convergent in a direction towards the aperture, and the substance depot is a solid body friction fitted between said convergent side walls.

19. The device of claim 18, wherein said substance depot is cylindrical, received in said side walls with its cylindrical axis extending towards the aperture, and having a convexly curved end surface protruding beyond the inner surface of the adhesive layer.

20. The device of claim 17, wherein the aperture through the inner end of each dimple is defined in part by a pair of opposed lips presented towards each other, and the substance depot is a solid body positively positioned between said lips, with an innermost surface protruding therebelow.

21. The device of claim 20, wherein the substance depot is spherical.

22. The device of claim 20 wherein the substance depot is cylindrical with a curved surface thereof protruding below said lips.

23. The device of claim 20 wherein the aperture through each dimple is further defined by a pair of convergent side walls.

24. The device of claim 23 wherein the substance depot is cylindrical, with a curved surface thereof protruding below said lips, and the end surfaces thereof friction fitted between said convergent side walls.

25. The device of claim 15 further including a layer of inert filler material interposed between the barrier sheet and the skin compatible adhesive.

26. The device of claim 25 wherein the inert filler material is closed cell foam plastic, and carries the skin compatible adhesive layer on its inner surface.

27. The device of claim 17 further including a lid adapted to attach to the dimpled sheet to cover the outer ends of said dimples and define a drug formulation receiving reservoir therewith.

28. The device of claim 27 wherein said dimpled sheet includes a planar lateral extension hingedly connected to the dimpled portion thereof, said lid being detachably secured to said lateral extension.

29. The device of claim 28 wherein said planar extension is detachable from the remainder of the dimpled sheet, after attachment of the lid to the dimpled sheet and removal of said lid from the planar extension.

30. A process of preparing a substance transfer device as claimed in claim 1, said process comprising:
providing a layer of skin compatible adhesive sandwiched between an upper release liner sheet and a lower release liner sheet;
perforating said release liners and skin adhesive layer with an array of channels in a predetermined pattern;
inserting into the channels so formed solid substance depots to lodge within the channels and to leave exposed a surface of the depot at the surface of one of said release liners.

* * * * *